United States Patent [19]

Leather

[11] Patent Number: 4,493,321

[45] Date of Patent: Jan. 15, 1985

[54] VENOUS VALVE CUTTER FOR THE INCISION OF VALVE LEAFLETS IN SITU

[76] Inventor: Robert P. Leather, Morehouse Corners Rd., Chatham, N.Y. 12037

[21] Appl. No.: 381,699

[22] Filed: May 25, 1982

[51] Int. Cl.³ ............................................. A61F 17/32
[52] U.S. Cl. ................................. 128/305; 128/303 R
[58] Field of Search .................. 128/305, 311, 303 R; 604/22

[56] References Cited

U.S. PATENT DOCUMENTS

| | | | |
|---|---|---|---|
| 1,167,014 | 1/1916 | O'Brien | 128/305 |
| 2,029,495 | 2/1936 | Lowe | 128/305 |
| 2,779,334 | 1/1957 | Sandborn | 128/303 R |
| 3,762,416 | 10/1973 | Moss et al. | 128/305 |
| 3,837,345 | 9/1974 | Matar | 128/305 |
| 4,273,128 | 6/1981 | Lary | 128/305 |
| 4,290,427 | 9/1981 | Chin | 128/305 X |

FOREIGN PATENT DOCUMENTS 2044103  10/1980  United Kingdom ................ 128/305

OTHER PUBLICATIONS

Kutz, C. M., Hendricks W. C., "New Vein Stripper and Technique of Stripping", Surgery, vol. 29, No. 2, pp. 271-275, 1951.

Peter B. Samuels, M.D. et al.—In Situ Saphenous Vein Arterial Bypass: "A Study of the Anatomy Pertinent To Its Use in Situ as a Bypass Graft with a Description of a New Venous Valvulatome"—The American Surgeon, Feb., 1986, vol. 34, No. 2—pp. 122-130.

E. Skagseth and K. V. Hall—"In Situ Vein Bypass"—Experiences with New Vein Valve Strippers—Scand J. Thor Cardiovasc Surg. 7:53-58, 1973.

Primary Examiner—William E. Kamm
Assistant Examiner—Christine A. Fukushima
Attorney, Agent, or Firm—Heslin, Watts & Rothenberg

[57] ABSTRACT

A blade is drawn by means of a rod attached centrally of its cutting edge so that a portion of the blade extends on either side of the rod. An elongate centering device precedes the blade and its protective encasement so as to ensure that the device will not engage side branches of the vein. A catheter follows the valve cutter so that fluid may be introduced into the vein to snap valves shut ahead of the cutting device. The assembly is drawn through a vein by a rod having sufficient torsional rigidity to permit controlled orientation of the blade for efficient engagement and cutting of valve leaflets.

27 Claims, 3 Drawing Figures

VENOUS VALVE CUTTER FOR THE INCISION OF VALVE LEAFLETS IN SITU

BACKGROUND AND SUMMARY OF THE INVENTION

This invention relates to the use of a valve cutter for preparing a vein in situ for an arterial bypass.

Revascularization of lower limbs threatened by ischemia has long presented a challenge for vascular surgeons. Any obstruction of the inflow of arterial blood to the lower limbs, e.g. by the narrowing of arteries by spasm or disease, presents an immediate limb threatening condition where if not reversed can ultimately lead to amputation. Various surgical techniques have been devised to bypass the damaged or obstructed artery in order to restore lower limb circulation. A brief survey of the surgical procedures presently available will serve to highlight the limitations of the current techniques.

Historically, the use of infrapopliteal arteries as outflow tracts for bypassing occluded proximal arteries has become a well-established surgical entity. The use of the saphenous vein in situ as a conduit for bypassing nonfunctional arteries is a theoretical ideal since it provides viable, untraumatized endothelium and closely matches the size of the artery to be bypassed therefore facilitating anastomosis. Moreover, its gradual taper results in optimum flow characteristics. However, the chief obstacle in directing the flow of blood in veins from the heart to the limbs is the presence of valves in the veins. Venous valves are so arranged that they allow free passage of blood toward the heart but impede or prevent passage of blood in the opposite direction. Most commonly, each valve is composed of two leaflets placed opposite each other and when a current of blood or fluid away from the heart occurs, their opposed edges are brought together and the current is interrupted. In order to obliterate the functioning of the venous valves, several procedures have been devised: excising a segment of the vein and reversing its position; using a vein prosthesis constructed of synthetic material; and removal or destruction of the venous valves. In actual practice all of the above have been attempted with varying degrees of success.

The first of the above procedures to be tried was excision and reversal of the saphenous vein. The technique remains the one most commonly used and the standard against which alternatives are measured. Meticulous preservation of the endothelial lining of the veins harvested during vascular surgery is undoubtedly one of the most important factors in determining patency rates following bypass procedures. The vein wall is extremely sensitive to such factors as handling, toxic chemicals, cessation of blood flow and reacts to most local stimuli by undergoing vigorous and prolonged contractions. In spite of strict attention to details of vein harvesting, preparation and storage, endothelium desquamation occurs within a few minutes. Ultimate recovery of this endothelium may take up to 24 weeks. The patency rate of excised and reversed vein grafts falls sharply in the first 6-12 months, probably a direct consequence of early endothelium damage.

The quest for an autogenous tube lined with normal endothelium led to the concept of using the saphenous vein in situ. Fracture of the venous valve was one of the first attempts to destroy the functioning of the valves. This technique, originally suggested and used over 20 years ago, produced inconsistent results, the best of which were no better than those obtained with saphenous vein reversal. This eventually led to its virtual abandonment by 1970.

The use of synthetic vein prostheses has met with controversy. Dacron was first used in the early attempts but was abandoned quickly because of a prohibitive failure rate in the femoro-popliteal position. Subsequent use of newer nonautogenous materials, e.g. polytetrafluoroethylene, has been reported, but again with unpredictable and even diametrically opposed results. The use of a vein prosthesis has one distinct albeit limited advantage and that is for the patient not having a healthy saphenous vein available for bypass. This, however, occurs infrequently in the patients that present for arterial bypass.

A method known as valve excision was developed about the same time valve fracture was being attempted. Valve excision produced consistently good results but for a variety of reasons never gained acceptance in the United States.

The concept of valve incision, the surgical technique for which the present invention was designed, was developed by this inventor in 1974 primarily as a means for preparing the saphenous vein for its use in situ as an arterial bypass. In principle, the preparation of the saphenous vein for such use entails removal of the valvular obstructions to distal arterial flow, interruption of the venous branches which become arteriovenous fistulae when the vein is arterialized and the mobilization of its ends for construction of the proximal and distal arterial anastomoses. The technical objective is to accomplish this with the minimum of operative manipulation. It has been found that the simplest, most expedient and least traumatic method of rendering the bicuspid venous valve incompetent is to cut the leaflets in their major axes while they are held in the functionally closed position by fluid flow or arterial pressure from above. This is the essence of the technique of valve incision.

Valve incision as it was performed prior to this invention involved introducing scissors of varying length through a proximal incision of the saphenous vein, closing the valve leaflets with an influx of fluid and then cutting the leaflets with the scissors. Valves down as far as the midthigh were incised by this route. The remainder of the valves were most readily incised by the use of a valvulotome which cuts each leaflet successively by retrograde passage through the distal incision. The in situ method appears to be ideal because of the superior stability of the endothelium and vein wall throughout the procedure.

The currently available instruments for accomplishing valve incision are of two main types, (1) scissors with blunted tips and a narrow shank and (2) valvulotomes. Several limitations are associated with the use of each type.

Visualization of the valve site is mandatory when either the scissors or valvulotomes are used since each instrument can be readily but accidentally introduced into the side branches which are present at all valve sites causing subsequent laceration of the vein wall. Visualizing each valve site during surgery can be very time consuming. The longer a vein is deprived of its blood supply, the higher the risk of endothelial damage. Therefore, time is of the essence.

Also, limited access is encountered with each of the above instrument types. The blunted tipped scissors can only extend from the proximal vein incision to about midthigh. The remainder of the valves must be incised by inserting the valvulotome through a suitably placed side branch or through a puncture produced distal to the valve site. This may entail numerous punctures along the vein wall with a resulting concomitant increase in potential trauma sites. The above methods are tedious, time-consuming, and demanding of superior surgical skills, thus severely limiting the use of the saphenous vein in situ. The use of my valve cutter, hereinafter described, is simple and less demanding of time and skill.

The aforementioned limitations led to the development of this invention. The valve cutter that is used for incision of valve leaflets is made of nontoxic and inert material. Its component parts include a leader sufficiently rounded as to prevent damage to the vein wall, a cutting blade that is enclosed in a protective support that is also tapered in order to facilitate passage up and down the inside of the vein without damaging the endothelium and a torsionally rigid, but flexible rod that connects the leader to the cutting blade. A first aperture is located in the leader that provides an attachment site for an extension rod that is used for orienting the position of the valve cutter while inside the vein. A second aperture is located in the cutting blade support that permits suturing of the valve cutter to a catheter which serves as a conduit for the influx of fluid into the vein during the actual cutting procedure. The pressure of this fluid forces the valve leaflets into a closed position so that the leaflets can be efficiently engaged by the cutting blade.

The method for using the valve cutter involves exposing both proximal and distal sites of the vein and artery to be used for the bypass. A proximal incision is made into the vein and the first two valves are cut with blunted tipped scissors while they are held in the closed position. A distal incision is made and a rod is inserted up the vein until it exits at the proximal incision site. The valve cutter is attached to the rod and the entire unit is then pulled down the vein. The fluid from the catheter keeps the valve leaflets closed during the cutting procedure. The valve cutter assembly is then returned to the proximal incision, the valve cutter is dismounted and the rod is removed from the distal incision. The remaining distal valves are severed by using a valvulotome inserted either through the distal incision or vein side branches.

The design of my valve cutter for the above procedure has the following advantages: visualization of each valve site is no longer necessary; there is little risk of accidentally introducing the valve cutter into the venal side branches and risking laceration; there is little risk of lacerating the vein wall; and no significant shearing or frictional forces are placed on the extremely sensitive endothelium. Most importantly, this invention permits use of the saphenous vein in situ in a great number of cases where that is not now possible. As a result, it can be expected that an increased number of successful revascularizations of lower limbs threatened by ischemia will result with a consequent improvement in limb salvage rates.

BRIEF DESCRIPTION OF THE DRAWINGS

The present invention will be more fully understood in view of the following description taken in conjunction with the accompanying drawings wherein.

DETAILED DESCRIPTION OF THE INVENTION

Figures 1, 2:
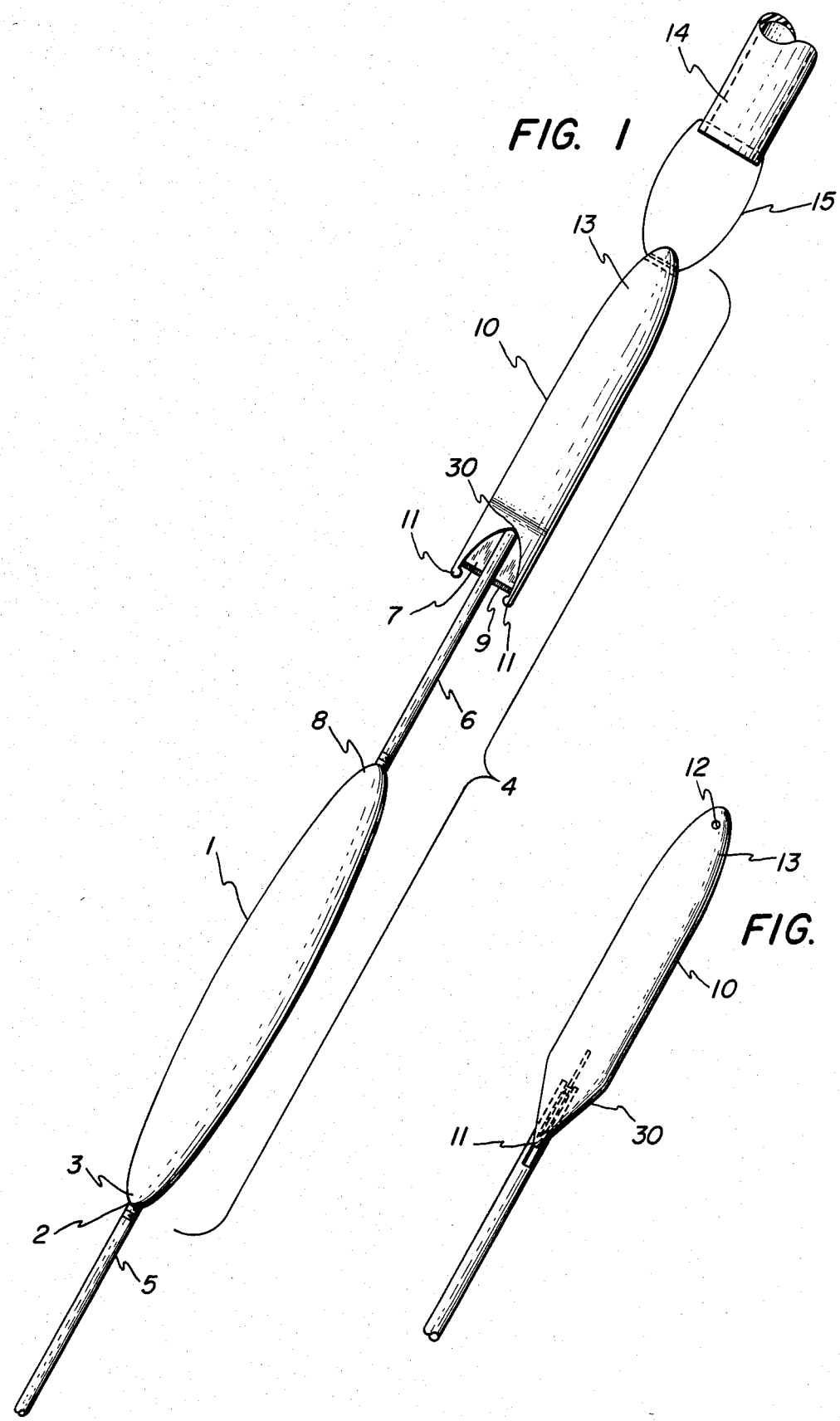
FIG. 1 is a top plan view showing my valve cutter in association with a preceding centering device and a following catheter.
FIG. 2 is a side view of my cutting device.

FIG. 1 shows an assembly of elements used with my invention. The assembly includes a leader 1 and blade support 10 with blade 7. These two elements are referred to collectively hereinafter as valve cutter 4. Leader 1 serves to center blade support 10 and blade 7 as valve cutter 4 passes through a vein. Also shown in the assembly of FIG. 1 is a catheter 14.

Leader 1 is molded with sufficient taper as to facilitate passage inside the vein with minimal risk of damage to the sensitive endothelium. A first threaded aperture 2 located at anterior end 3 of leader 1 and extending inward for a limited distance provides a means for attaching leader 1 to a first rod 5. First rod 5 should be flexible, but must be of sufficient torsional rigidity to permit controllable rotation of valve cutter 4. First rod 5 extends from the distal vein incision and can be rotated manually to change the angle of cutting blade 7. First rod 5 also provides a means for moving valve cutter 4 down the vein so that the valve leaflets will be severed. A second rod 6, again flexible, but sufficiently torsionally rigid, connects posterior end 8 of leader 1 with cutting edge 9 on each side of cutting blade 7 and may be joined to cutting blade support 10. Cutting blade support 10 is also of sufficient taper as to minimize contact with the vein wall. It is important that the valve leaflets do not slip off the cutting blade 7. Cutting blade support 10 extends forwardly of cutting edge 9 to form two curved protrusions or guards 11 with sufficient inward curvature as to prevent such slipping. Guards 11 also serve to protect the vein wall from any contact with cutting edge 9. Second aperture 12 located at posterior end 13 of cutting blade support 10 provides for attachment of catheter 14 with suture material 15.

The materials used for the construction of valve cutter 4 components may be of any suitable type for the purposes indicated and are preferably inert and nontoxic. The dimensions of valve cutter 4 are limited solely by the size of vein used for bypass. Blade 7 is encased within blade support 10 in any conventional manner. Support 10, for example, may be molded of any suitable material so that blade 7 may be rigidly mounted therein.

It will be observed from FIG. 2 that the forward or cutting end of blade support 10 is tapered from the rearmost point 30 of its blade opening to guards 11. This tapering serves to facilitate passage of support 10 through the vein and through a valve being cut.

DETAILED DESCRIPTION OF VEIN PREPARATION FOR BYPASS

Prior to surgery, an invaluable aid in the performance of this procedure is the routine use of saphenous phlebography. This accurately portrays the frequently encountered anatomic variations of this vein. If unrecognized, these variations may lead to frustrating as well as largely ineffectual surgical explorations resulting in failure or abandonment of the procedure. In addition, the path of the greater saphenous vein below the knee is marked on the skin before the operation with the patient in the standing position. This is done by introducing a pressure wave proximally by tapping or brushing the distended vein and detecting the wave which is propagated by palpation or by Doppler ultrasound of the vein if it is too deeply placed beneath the skin.

A simultaneous distal and proximal exposure of both artery and vein can be accomplished with a two team approach. The distal saphenous vein is exposed by an incision parallel to and posterior to the position of the vein as previously determined, at the level of the anticipated distal arterial anastomosis. Its size is determined by in situ comparison with catheters of known size or by measurement with a sterile Vernier caliper. A minimal diameter of 2.5 mm is considered to be acceptable. From the proximal incision the saphenofemoral junction valve is excised completely. A second valve is present 3 to 5 cm distal from proximal incision and a third valve at 10 cm, either immediately at or distal to the medial accessory branch. These valves are identified by gently distending the vein through the proximal incision with an intravenous solution. These valves are cut with blunted tip scissors. The plane of the valve leaflets is normally parallel to the skin.

Figure 3:
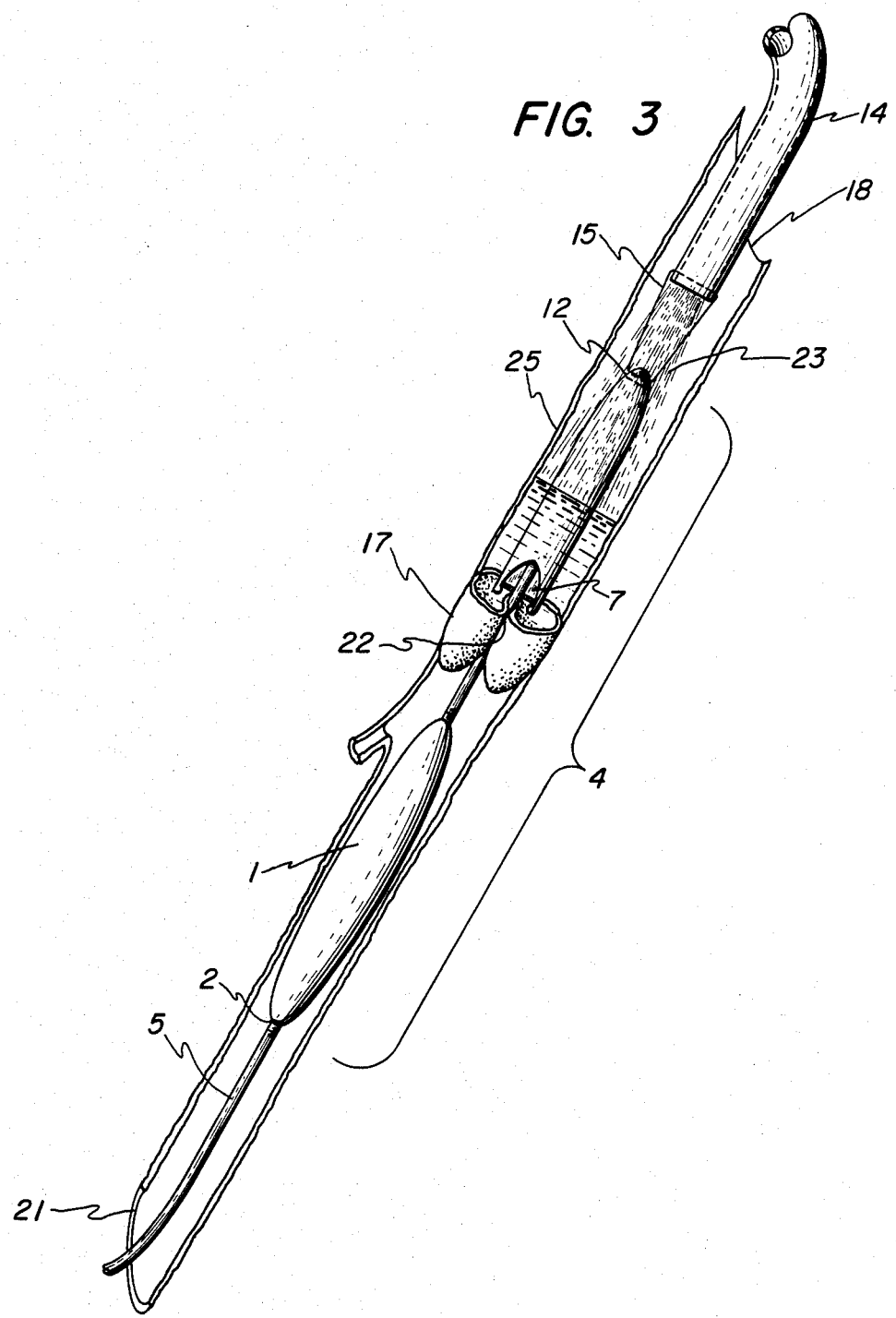
FIG. 3 illustrates the invention during use within a vein.

Referring now to FIG. 3 in actual practice a rod or a Fogarty catheter may be introduced into the saphenous vein 25 below the knee via a distal incision 21 made in one of the side branches and passed proximally to exit through the proximal incision 18. Any sufficiently torsionally rigid rod 5 can be used that permits rotational orientation of all instruments with relation to valve leaflets 22. Rod 5 is attached to valve cutter 4 via threaded first aperture 2 located in leader 1. Valve cutter 4 is then drawn slowly down the vein with plane of cutting blade 7 oriented 90° to plane of closure of a valve 17 to be cut. Simultaneously, intravenous fluid 23 is introduced via the proximal incision 18 from catheter 14.

Fluid 23 is regulated at 200 mm Hg pressure by a pneumatic transfusion cuff on a plastic bag containing fluid 23. The pressurized fluid column snaps each successive valve into the closed position so that leaflets 22 are efficiently engaged by cutting blade 7. Catheter 14 is attached to valve cutter 4 by sutures 15 through second aperture 12. Valve cutter 4 is advanced to the knee provided the vein is large enough to accommodate it, then withdrawn through proximal incision 18 and dismounted. First rod 5 is removed from the distal incision 21 and the remaining valves are cut with a valvulotome introduced from either the distal incision 21 or a side vein branch. While the invention has been particularly shown and described with reference to the preferred embodiment thereof, it will be understood by those skilled in the surgical art that various changes in form and detail may be made therein without departing from the true spirit and scope of the invention as defined by the appended claims.

What is claimed is:

1. A device for cutting venous valves comprised of:
   an elongate support member having a forward end and a rearward end and adapted to pass through a vein forward end first;
   a blade having a cutting edge running between two ends and mounted on the forward end of the support member with said cutting edge exposed and facing in the direction of intended movement through a vein; and
   means connected to the blade substantially midway between its ends for drawing it through a vein with a portion of its cutting edge exposed on either side of said means,
   whereby to cut valve leaflet pairs as the device is drawn through a vein.

2. The invention of claim 1 further including means for maintaining the engagement between a leaflet and the blade as the former is being cut,
   whereby to prevent a valve leaflet from slipping off the blade as the cutting device passes.

3. The invention of claim 2 wherein the engagement maintenance means is comprised of a guard at each end of the cutting edge extending from the support member so as to protrude forwardly of said cutting edge.

4. The invention of claim 1 wherein the drawing means includes means for controlling the rotational orientation of the blade within a vein.

5. The invention of claim 1 in combination with means for closing a valve as the same is approached by the cutting device.

6. The invention of claim 5 wherein the valve closing means is comprised of a catheter attached to the cutting device so as to follow it when the device is passed through a vein, said catheter being adapted to emit a fluid within the vein.

7. The invention of claim 1 wherein the rearward end of the support member is adapted to be connected to a catheter.

8. A device for cutting venous valve leaflet pairs comprised of:
   an elongated cutting member having a forward end and a rearward end and adapted to pass through a vein forward end first without making continuous circumferential contact with the walls thereof, said cutting member having an exposed cutting blade on its forward end facing in the direction of intended movement through a vein;
   elongate body means connected by a first rod to the cutting member at its forward end centrally of the cutting blade for centering the cutting member in a vein with its blade sufficiently exposed about the rod to cut enountered valve leaflet pairs as the cutting member is drawn through them; and
   means including a second rod connected to the centering means for drawing the centering means and the cutting member through a vein.

9. The invention of claim 8 in combination with means for closing a valve as the same is approached by the cutting device.

10. The invention of claim 9 wherein the valve closing means is comprised of a catheter adapted at one end for connection to a fluid supply source and attached at its other end to the cutting device so as to follow it when the device is passed through a vein.

11. The invention of claim 8 further including means for detaching the drawing means from the cutting means.

12. The invention of claim 8 wherein the cutting blade has a substantially straight cutting edge.

13. The invention of claim 12 further including means for maintaining the engagement between a leaflet and the cutting blade as the former is being cut.

14. The invention of claim 13 wherein the rods and their connections to the centering means and the cutting member are all sufficiently torsionally rigid to permit controllable rotational orientation of the blade within a vein by rotation of the rod.

15. A venous valve cutting device for rendering valves inoperative comprising:

means adapted to be passed through a vein for cutting venous valves in their functionally closed position as it passs; and means attached to the cutting means for introducing a fluid into the vein so as to operate a valve to its functionally closed position as the same is approached by the cutting means.

16. The invention of claim 15 wherein the fluid introducing means is comprised of a catheter attached to the cutting device so as to follow it when the device is passed through a vein, said catheter being adapted to emit a fluid within the vein.

17. The invention of claim 15 wherein the cutting means includes means for connecting it to means for drawing it through a vein.

18. The invention of claim 17 in combination with means for drawing the cutting means through a vein.

19. Apparatus for disabling venous valve leaflet pairs comprised of:

a cutting member adapted to be passed through a vein axially in either direction, said member being adapted to cut valve leaflet pairs as they are encountered while passing them in at least one direction;

first means detachably connected to the cutting member at one end for drawing it axially through a vein in one direction; and second means connected to the cutting member at its other end for drawing it axially through a vein in the opposite direction.

20. The apparatus of claim 19 in which the second drawing means is a catheter adapted to emit a fluid within the vein for closing valves as they are approched by the cutting member.

21. The invention of claim 20 wherein the first drawing means includes a rod connected to the cutting member and an elongated leader member connected to the rod for centering the cutting member in the vein.

22. The apparatus of claim 21 wherein the cutting member is comprised of an elongated support member having a cutting edge exposed sufficiently on one end for cutting valve leaflet pairs in their closed position and having its other end adapted to be connected to a catheter.

23. A device for cutting venous valve leaflet pairs comprised of:

an elongated cutting member having a forward end and a rearward end and adapted to pass through a vein axially in either direction without making continuous circumferential contact with the walls thereof, said cutting member having an exposed cutting blade on its forward end and said cutting member being adapted or attachment with a drawing means at its rearward end;

a rod connected at its one end to the cutting member at its forward end centrally of the cutting blade for drawing the cutting member through a vein with its blade sufficiently exposed about the rod to cut encountered valve leaflet pairs as the device passes through them; and means connected to the rod at its other end for centering the rod and the cutting member in a vein and preventing the cutting member from engaging side branches of a vein, said centering means being adapted for attachment with a drawing means.

24. The invention of claim 23 wherein the centering means is an elongated body.

25. The invention of claim 24 wherein the cutting blade has a substantially straight cutting edge running between two ends.

26. The invention of claim 25 further including means for maintaining the engagement between a leaflet and the cutting blade as the former is being cut, whereby to prevent a valve leaflet from slipping off the blade as the cutting device passes.

27. The invention of claim 26 wherein the engagement maintenance means is comprised of a guard at each end of the cutting edge extending from the support member so as to protrude forwardly of said cutting edge.

* * * * *